(12) United States Patent
Graf

(10) Patent No.: US 7,935,132 B2
(45) Date of Patent: May 3, 2011

(54) INTERVERTEBRAL LINKING DEVICE

(75) Inventor: Henry Graf, Lyons (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 772 days.

(21) Appl. No.: 11/853,538

(22) Filed: Sep. 11, 2007

(65) Prior Publication Data
US 2008/0058809 A1   Mar. 6, 2008

Related U.S. Application Data

(63) Continuation of application No. 10/760,142, filed on Jan. 16, 2004, now abandoned, which is a continuation of application No. PCT/FR02/02593, filed on Jul. 19, 2002.

(51) Int. Cl.
*A61B 17/58* (2006.01)
*A61B 17/80* (2006.01)
*A61B 17/86* (2006.01)

(52) U.S. Cl. ........ 606/246; 606/280; 606/281; 606/283; 606/286; 606/287; 606/288; 606/289; 606/290; 606/291

(58) Field of Classification Search .................. 606/280, 606/281, 286, 287, 283, 288–291, 902–906
See application file for complete search history.

(56) References Cited

U.S. PATENT DOCUMENTS

| | | | | | |
|---|---|---|---|---|---|
| 3,003,399 | A | * | 10/1961 | Donner | 89/37.13 |
| 4,834,518 | A | * | 5/1989 | Barber | 359/375 |
| 5,057,111 | A | * | 10/1991 | Park | 606/288 |
| 5,607,426 | A | * | 3/1997 | Ralph et al. | 606/287 |
| 5,735,853 | A | * | 4/1998 | Olerud | 606/71 |

* cited by examiner

*Primary Examiner* — Thomas C Barrett
*Assistant Examiner* — Sameh Boles

(57) ABSTRACT

One embodiment includes at least a fixed element designed to be secured to a vertebra or sacrum, at least a mobile linking element and at least an intermediate element that articulates the mobile element relative to the fixed element. The intermediate element is received in an internal volume of the mobile element and is deformable, so as to be introduced by impingement into the inner volume. The fixed element is received at least partly in an internal volume of the intermediate element and has a position for use wherein said fixed element has three degrees of freedom in rotation, but is linked in translation, relative to the intermediate element.

25 Claims, 3 Drawing Sheets

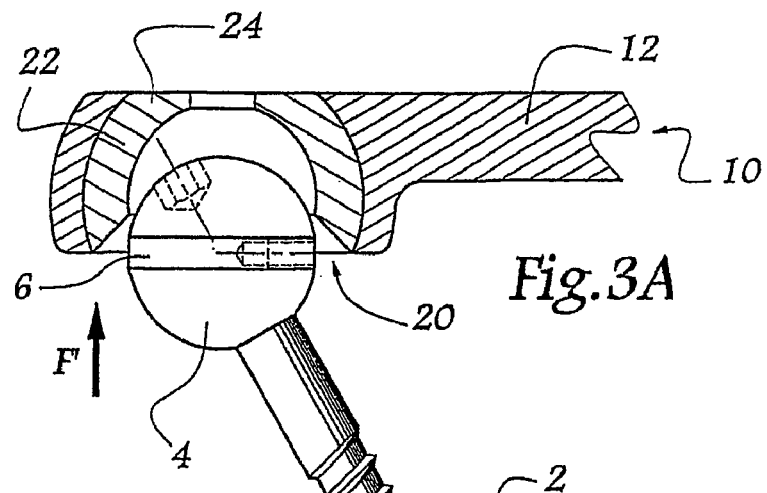
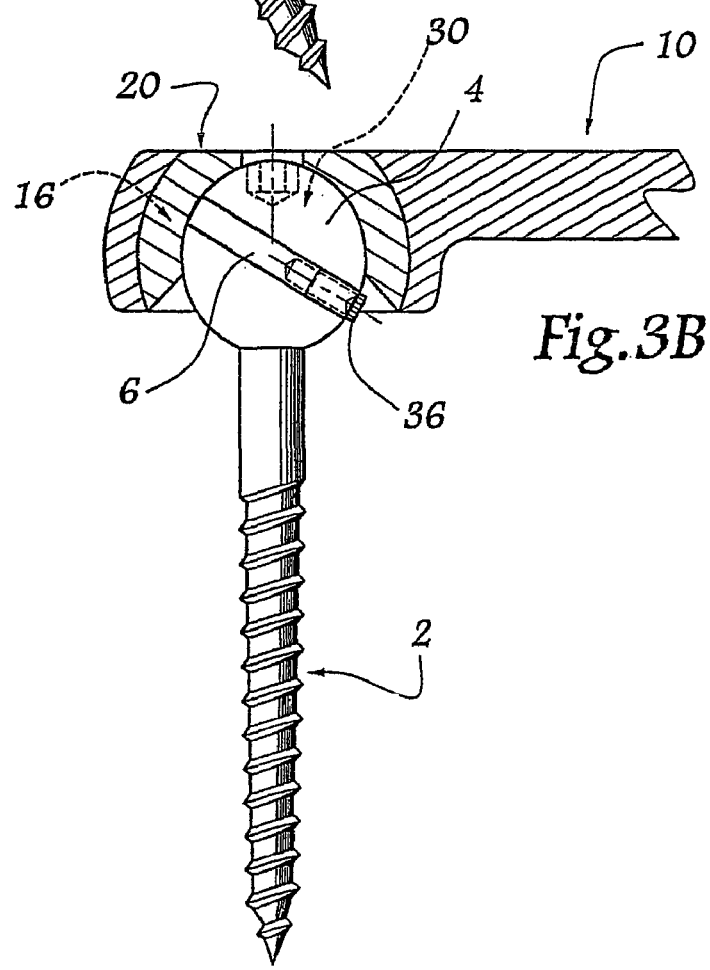

INTERVERTEBRAL LINKING DEVICE

CROSS-REFERENCE TO RELATED APPLICATION

The present application is a continuation patent application of U.S. patent application Ser. No. 10/760,142 filed Jan. 16, 2004 now abandoned entitled INTERVERTEBRAL LINKING DEVICE, which is a continuation of an International Patent Application PCT/FR02/02593 filed Jul. 19, 2002 entitled INTERVERTEBRAL LINKING DEVICE, which claims priority to French Patent Application No. 0109773 filed Jul. 20, 2001, all of which are hereby incorporated by reference.

SUMMARY OF THE INVENTION

The present invention relates to an intervertebral linking device.

Such a device is known which comprises at least two pedicular screws, each of which has a first end secured to a corresponding vertebral body, a bulging intermediate portion, and a second, threaded, end. Auxiliary members, provided with an arch for fastening a rod extending between the vertebrae, are located on each of the above-mentioned bulging portions. A bolt co-operating with the threaded end of each screw enables each auxiliary member to be immobilised, once that member has been put in place, in an appropriate manner.

However, this known device has some disadvantages in that it involves a relatively delicate mounting process. In addition, once implanted, it does not offer any degree of freedom between the various elements constituting it. Thus, when forces are exerted in the region of the vertebral bodies, the absence of a degree of freedom brings about a transmission of these forces onto the whole of the device, so that the device has a tendency to become separated from the vertebrae which it connects, and also brings about dysfunctions in the entire vertebral chain.

In order to overcome those various disadvantages, the present invention proposes to provide a device whose structure is simple, whose mounting is easy and which is reliably implanted in the vertebrae which it connects.

To that end, the invention relates to an intervertebral linking device which is to connect at least two vertebrae to one another, characterised in that it comprises:

at least one fixed element which is to be secured to a vertebra or to the sacrum, at least one mobile linking element suitable for being displaced relative to the or each fixed element, and also at least one intermediate element permitting the articulation of the or each mobile element relative to the or each fixed element, in that the or each intermediate element is received, in use, in an internal volume of the mobile element, or of the fixed element, the intermediate element being deformable so that it can be introduced by impaction into that internal volume, and in that the fixed element, or the mobile element, is received at least partially, in use, in an internal volume of the intermediate element, the fixed element or the mobile element having, with the intermediate element, a mutual position of use in which the fixed element or the mobile element, has three degrees of freedom in rotation, but is linked in translation, relative to the intermediate element, and a mutual position of introduction in which the fixed element, or the mobile element, has three degrees of freedom in rotation and in translation relative to the intermediate element.

According to other features of the invention:

the intermediate element assumes the form of a cup;

the internal volume of the intermediate cup is bordered by a truncated spherical surface;

the intermediate cup has a truncated spherical external surface which is concentric with the internal surface;

the internal and external surfaces define a wall of the intermediate cup;

the thickness of the wall is from 0.5 to 3 mm, preferably from 1 to 1.5 mm;

the intermediate element is produced from polyethylene.

DESCRIPTION OF THE DRAWINGS

The invention will be described hereinafter with reference to the appended drawings which are given purely by way of non-limiting example and in which:

FIGS. 3A and 3B are views analogous to FIG. 1 illustrating the introduction of a fixed element of the device of FIG. 1 into the internal volume of the intermediate element.

DESCRIPTION OF THE ILLUSTRATED EMBODIMENTS

Figure 1:
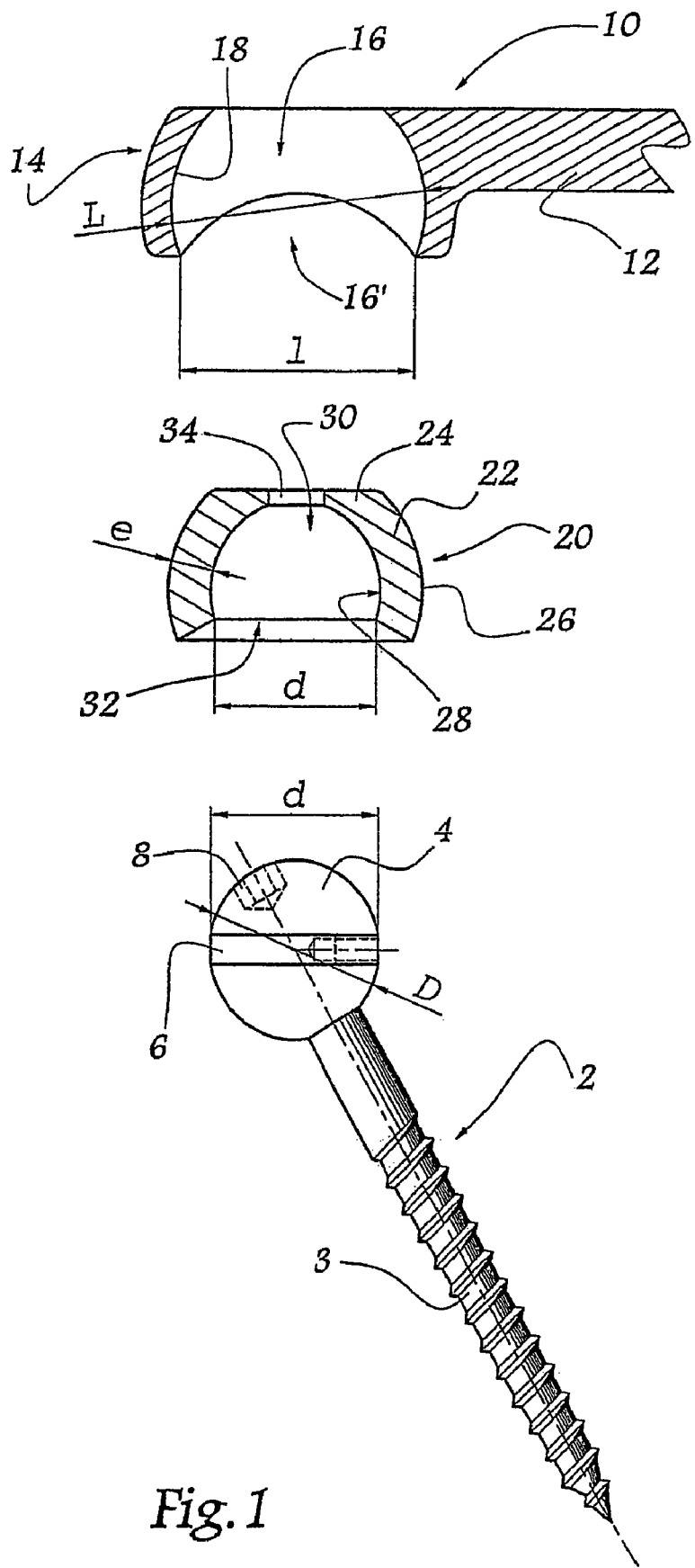
FIG. 1 is a view in longitudinal section illustrating the various elements constituting an intervertebral linking device according to the invention.

The linking device illustrated in FIG. 1 comprises a pedicular screw 2 which is to be secured in a vertebral body (not shown).

This pedicular screw, which constitutes a fixed element of the linking device, is provided with a rod 3 terminated by a spherical head 4 which comprises an equatorial flat portion 6. The latter extends in an inclined manner to the effect that it is not perpendicular to the principal axis A of the screw 2.

The head 4 is also hollowed out, on the opposite side to the rod 3, with a blind hole 8. The latter is to receive a control device (not shown) which is, for example, the end of a screwdriver or of a hexagonal key.

The linking device of FIG. 1 also comprises a mobile element which is illustrated partially and which is generally indicated by the reference 10. This element has a body 12 which extends between the two vertebrae that are to be connected by the device of the invention. This body is terminated by two hollow ends, only one of which, 14, is shown.

Each end defines a housing 16 which constitutes an internal volume of the element 10 and which is bordered by internal surface 18 forming a portion of a sphere. The transverse dimension 1 of the opening 16' of the housing 16 is smaller than the diameter L of the housing.

Finally, the device of FIG. 1 comprises an intermediate element 20 which constitutes a cup. The cup, which has a truncated hemispherical shape, has a thin wall 22 which extends from a base 24 of the cup.

The external surface 26 of the wall 22 delimits a portion of a sphere, the diameter of which is identical to that L of the housing 16. In addition, the internal surface 28 of the wall 22, which forms an internal volume 30 of the cup 20, has a diameter D identical to that of the head 4.

Furthermore, the transverse dimension d of the opening 32 of the internal volume 30 is equal to that of the flat portion 6 of the head 4. The opening is more "narrow" than the internal volume inasmuch as the spherical internal surface 28 extends at an angle of more than 180°.

Finally, the base 24 of the cup 20 is hollowed out with an orifice 34 permitting the passage of a control tool in the direction towards the blind hole 8 of the pedicular screw 2.

It should be noted that the cup 20 is produced from a deformable material, such as polyethylene. This feature, in association with the thinness of the wall 22, enables the cup 20 to be introduced by impaction into the housing 16 of the mobile element 10. The thickness e of the wall 22 is, for example, from 0.5 to 3 mm, preferably from 1 to 1.5 mm.

The mounting of the linking device illustrated in FIG. 1 will now be described with reference to FIGS. 2A, 2B, 2C, 3A and 3B.

First of all, the cup 20 has to be introduced into the internal volume 16 of the mobile element 10.

Figure 2C:
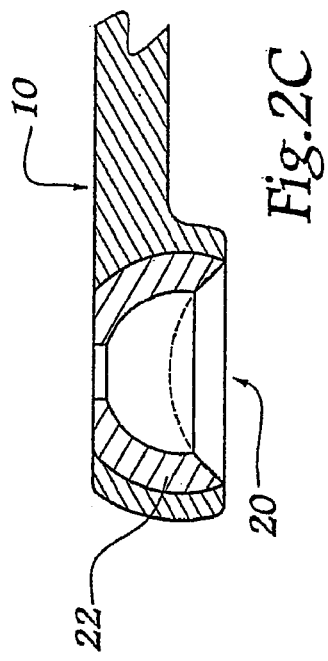
FIGS. 2A, 2B and 2C are views analogous to FIG. 1 illustrating two steps in the mounting of an intermediate element of the device of FIG. 1 in the internal volume of a mobile element of that device.
Figure 2B:
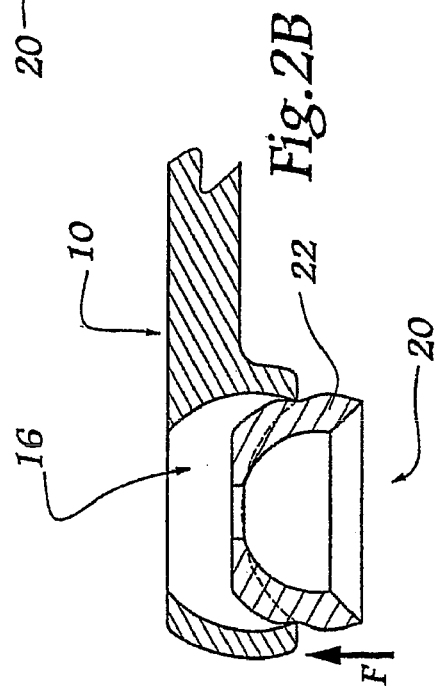
Figure 2A:
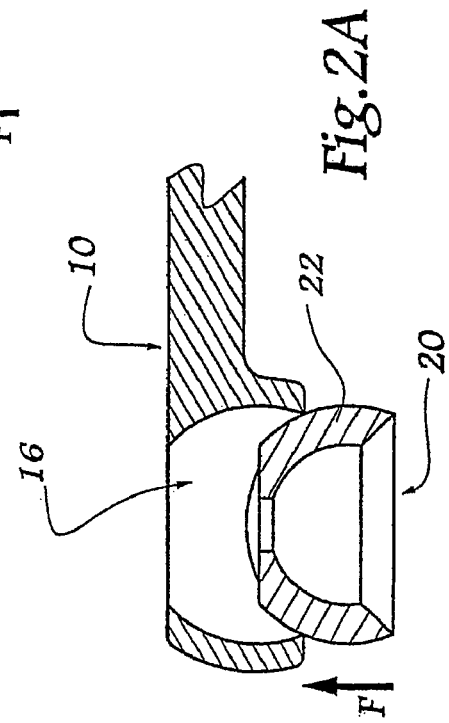

For that purpose, as shown in FIG. 2A, the cup 20 is disposed in such a manner that it is facing the housing 16. Subsequently, it is brought axially closer to the mobile element 10, in accordance with the arrow F.

Given that the cup 20 is resiliently deformable, its transverse dimensions, in particular the inside diameter D of its wall 22, are capable of undergoing a momentary reduction. This therefore enables the cup 20 to be introduced by impaction in accordance with the arrow F into the housing 16 of the mobile element 10 (FIG. 2B).

Once that operation has been carried out, as shown in FIG. 2C, the external surface 26 of the thin wall 22 extends in contact with the internal surface 18 of the housing 16, having the same diameter. Thus, the cup 20 has three degrees of freedom in rotation relative to the mobile element.

On the other hand it has no degree of freedom in translation relative to the element 10 in this position of use, since the periphery of the opening 16', the transverse dimension of which is smaller than the diameter of the housing 16, prevents the cup 20 from coming out of the housing again.

It is then necessary to introduce the spherical head 4 of the screw 2 into the internal volume 30 of the cup 20.

For that purpose, the screw 2 is first of all inclined in such a manner that the flat portion 6 extends horizontally in FIG. 3A, that is to say, perpendicularly to the principal axis of the cup 20. The cup 20 is then brought closer to the screw 2 in accordance with a translation parallel with the principal axis of the cup 20 (arrow F').

Given that the transverse dimension of the flat portion is equal to that d of the opening 32 of the internal volume 30, this enables the head 4 to be freely introduced into the internal volume.

Subsequently, the head 4 is pivoted inside the internal volume in such a manner that the flat portion 6 is no longer facing the above-mentioned opening 32. In this position of use (FIG. 3B), the head 4 is free to pivot relative to the internal volume 30 but has no degree of freedom in translation relative to the cup 20.

The diameter D of the head 4 is larger than the transverse dimension of the opening 32. In addition, the periphery of the opening 32 is rendered substantially rigid owing to the presence of the rigid walls of the mobile element 10. Thus it is almost impossible for the periphery of the opening 32 to be deformed radially, which prevents the head 4 from coming out of the internal volume 30 again.

Once the device has been placed in the configuration of FIG. 3B, it is necessary to fix the pedicular screw 2 in a corresponding vertebral body by means of a control device co-operating with the blind hole 8.

By way of a variation in mounting, it is possible first of all to fix each pedicular screw in a corresponding vertebral body.

Then each cup 20 is introduced into a corresponding housing 16 of the mobile element, as explained in FIGS. 2A to 2C.

The fixed element and the mobile element are then brought closer to one another and the cup 20 is caused to tilt within its housing 16. This tilting may be effected by means of a rod (not shown) forming a probe which comes into contact with the base 24 of the cup 20 from the orifice of the housing 16 opposite the pedicular screw 2.

Finally, the intermediate element 20 so tilted is brought closer, relative to each screw 2, so that each flat portion 6 can permit the introduction of a corresponding screw into the internal volume 30.

Once the device of the invention has been placed in the configuration of FIG. 3B, it is possible to fit onto the flat portion 6 an advantageously removable stop means, such as a screw 36. The latter, by limiting the pivoting of the head 4 relative to the cup 20, prevents the head from recovering its position in FIG. 3, which avoids any inadvertent separation between the cup 20 and the screw 2.

The invention is not limited to the example described and represented.

Thus, the intermediate cup 20 may be received in a housing with which the pedicular screw, and not the mobile element, is equipped. Under those conditions, the mobile element then has a spherical head, similar to the head 4, suitable for being introduced into the internal volume of the intermediate cup.

Furthermore, the screw 2, the mobile element 10 and the intermediate cup 20 are capable of having other arrangements, such as those described in French Patent Application 00 08522, filed on 30 Jun. 2000 by the present Applicant, and also those described in International Patent Application PCT-FR-01/02098, filed on 29 Jun. 2001 by the present Applicant.

The invention enables the objectives mentioned above to be achieved.

The various elements constituting the intervertebral linking device of the invention have a relatively simple structure.

The assembly of these elements is particularly easy for the surgeon because the intermediate element can be introduced by impaction into the internal volume of the mobile element, or of the fixed element.

Then, the presence of the intermediate element permits the mutual mounting of the fixed and mobile elements, even if there is practically no clearance in rotation between those two elements.

Moreover, it should be noted that, even though the intermediate element is deformable, which facilitates the mounting thereof, it becomes substantially rigid once introduced into its housing. This rigidity, which is conferred on it by the rigid walls of the housing, provides satisfactory stability for the device, once implanted.

Thus the device has a high degree of resistance in respect of mechanical stresses exerted, in particular, in traction. In addition, the presence of the intermediate element allows any forces to which the linking device of the invention is subjected to be transmitted only to a very slight extent.

The invention claimed is:

1. Intervertebral linking device to connect at least two bones of the spine to one another, comprising:
   at least one fixed element which is to be secured to a vertebra of the spine or to a sacrum of the spine,
   at least one mobile linking element suitable for being displaced relative to the or each fixed element,
   at least one intermediate element permitting the articulation of each mobile linking element relative to the at least one fixed element at least at the time of assembly and implantation in the bone, wherein each intermediate element is received in an internal volume of a corresponding one of the at least one mobile linking element, or of a corresponding one of the at least one fixed element, the intermediate element being deformable to be placed into the internal volume by impaction, and wherein the at least one fixed element, or the at least one mobile linking element, is received at least partially in an internal volume of the intermediate element having a mutual position of use with three degrees of freedom in rotation at least at the times of assembly and implantation in the bone relative to the intermediate element while remaining linked in translation and a mutual position of introduction in which the corresponding one of the at least one fixed element, or the corresponding one of the at least one mobile element, has three degrees of freedom in rotation and in translation relative to the intermediate element at least at the times of assembly and implantation in the bone.

2. The device according to claim 1, wherein the intermediate element assumes the form of a cup.

3. The device according to claim 2, wherein the internal volume of the intermediate cup is bordered by a truncated spherical surface.

4. The device according to claim 3, wherein the intermediate cup has a truncated spherical external surface, which is concentric with the internal surface.

5. The device according to claim 4, wherein the internal surface and the external surface define a wall of the intermediate cup.

6. The device according to claim 5, wherein the thickness of the wall is from 1 to 1.5 mm.

7. The device according to claim 1, wherein the intermediate element is produced from polyethylene.

8. The device according to claim 1, wherein said internal volume is at least part spherical having an internal diameter, and said internal volume has an opening with a width smaller than said internal diameter, and wherein said intermediate element has an external diameter that is substantially the same as said internal diameter of said internal volume, such that when said intermediate element is inserted into said internal volume, said opening prevents said intermediate element from falling out of said internal volume.

9. The device according to claim 1, wherein said intermediate element has an internal volume having an internal diameter and an opening to said internal volume having a width less than said internal diameter, and said fixed element has a spherical head with an equatorial flat portion, said spherical head having a diameter between spherical surfaces that is substantially the same as said internal diameter, and said equatorial flat portion has a diameter that is substantially equal to said width of said opening.

10. The device according to claim 9, wherein said fixed element is a screw having a shaft with a longitudinal axis, and said flat surfaces do not intersect said axis.

11. The device of claim 9, wherein said spherical head has an equator of greatest diameter and said equatorial flat portion passes through said equator.

12. The device of claim 9, wherein said fixed element has a longitudinal axis and said equatorial flat portion resides in a plane oblique to said longitudinal axis.

13. The device according to claim 1, wherein said linking member is separated from at least one of the bones by the at least one fixed element.

14. An orthopedic surgical apparatus for connection to two adjacent vertebrae, comprising:

an elongated link member having a first end and a second end and a body extending between said ends, said first end having an upper surface and a lower surface and an internal volume bordered by walls forming a portion of a sphere, said internal volume terminating in an upper opening in said upper surface and a lower opening in said lower surface, said internal volume having a diameter, and said lower opening having a width that is smaller than said diameter of said internal volume;

a socket member made of a material that is resiliently deformable, said socket member having an external surface that is a portion of a sphere having a diameter substantially the same as said diameter of said internal volume, said socket member further having an internal surface that forms a portion of a spherical internal volume having an internal diameter, a base portion with an orifice through it and communicating with said internal volume of said socket member, and an opening opposite said base portion having a width that is smaller than said internal diameter of said socket member; and a screw having a head and a threaded shaft, said shaft extending along a longitudinal axis, said head being spherical and including an equatorial flat portion, said head having a first diameter between spherical portions and a second diameter between parts of said equatorial flat portion that is less than said first diameter, said first diameter being substantially the same as said internal diameter of said socket member, and said second diameter being substantially the same as said width of said socket member opening, wherein said socket member is inserted into said internal volume of said first end of said linking member, said socket being rotatable at least at the times of assembly and implantation in bone within said first end with three degrees of freedom but is prevented from falling out of said first end, and said screw head is inserted into said internal volume of said socket member, said screw head being rotatable at least at the times of assembly and implantation in bone within said socket member with three degrees of freedom but is prevented from falling out of said socket member.

15. The apparatus of claim 14, wherein said equatorial flat portion is in a plane that is not perpendicular to said shaft axis of said screw.

16. The apparatus of claim 14, wherein said socket member has an original shape, and said socket member deforms when inserted into said first end, and resumes said original shape when within said internal volume of said first end.

17. The apparatus of claim 14, wherein said screw head includes a hole in said equatorial flat portion, and further comprising a stop inserted in said hole so that a portion of said stop extends above said equatorial flat portion.

18. The apparatus of claim 17, wherein said stop is a set screw.

19. The apparatus of claim 14, wherein said second end has an upper surface and a lower surface and an internal volume bordered by walls forming a portion of a sphere, said internal volume of said second end terminating in an upper opening in said second end upper surface and a lower opening in said second end lower surface, said internal volume of said second end having a diameter, and said second end lower opening having a width that is smaller than said diameter of said internal volume of said second end;

a second socket member made of a material that is resiliently deformable, said second socket member having an external surface that is a portion of a sphere having a diameter substantially the same as said diameter of said internal volume of said second end, said second socket member further having an internal surface that forms a portion of a spherical internal volume having an internal diameter, a base portion with an orifice through it and communicating with said internal volume of said second socket member, and an opening opposite said second socket member base portion having a width that is smaller than said internal diameter of said second socket member; and a second screw having a head and a threaded shaft, said shaft extending along a longitudinal axis, said head being spherical and including an equatorial flat portion, said head having a first diameter between spherical portions and a second diameter between parts of said equatorial flat portion that is less than said first diameter, said first diameter being substantially the same as said internal diameter of said socket member, and said second diameter being substantially the same as said width of said socket member opening, wherein said socket member is inserted into said internal volume of said first end of said linking member, said socket being rotatable within said first end with three degrees of freedom but is prevented from falling out of said first end, and said screw head is inserted into said internal volume of said socket member, said screw head being rotatable within said socket member with three degrees of freedom but is prevented from falling out of said socket member.

20. The apparatus of claim 14, wherein said spherical head has an equator of greatest diameter and said equatorial flat portion passes through said equator.

21. An intervertebral linking device, comprising:
an elongated linking member having a first receiving portion, a second receiving portion and a body extending between said portions, said first receiving portion having an upper surface and a lower surface and an internal volume defined by a truncated spherical surface, said internal volume having an upper opening in said upper surface and a lower opening in said lower surface, each of said openings having a diameter, said internal volume having a maximum diameter between said openings, wherein said diameters of said upper and lower openings are smaller than said maximum diameter;

an intermediate member having a top surface and a bottom surface and a truncated spherical external surface, said truncated spherical external surface having a top diameter at said top surface, a bottom diameter at said bottom surface and a maximum diameter between said top and bottom surfaces, wherein said top and bottom diameters are smaller than said maximum diameter of said truncated spherical external surface, wherein said intermediate member includes an internal volume with a spherical portion defined by a truncated spherical internal surface, said internal volume having an upper opening in said upper surface and a lower opening in said lower surface and a maximum diameter between said upper and lower openings, each of said openings having a diameter, said maximum diameter of said internal volume of said intermediate member being larger than said diameters of said upper and lower openings of said internal volume of said intermediate member, wherein said maximum diameter of said truncated spherical external surface is larger than said diameters of said upper and lower openings of said internal volume of said elongated linking member; and a screw having a head and a threaded shaft, said shaft extending along a longitudinal axis, said head being spherical with an equator of greatest diameter and including an equatorial flat portion passing through said equator, said equatorial flat portion lying oblique to said longitudinal axis, said head having a first diameter between spherical portions and a second diameter between parts of said equatorial flat portion that is less than said first diameter, said first diameter being substantially equal to said maximum diameter of said internal volume of said intermediate member, said first diameter being larger than said diameter of said lower opening of said internal volume of said intermediate member, and said second diameter being equal to said diameter of said lower opening of said internal volume of said intermediate member;

wherein said intermediate member is inserted into said internal volume of said elongated linking member, said intermediate being rotatable at least at the times of assembly and implantation in bone within said internal volume with three degrees of freedom, and said screw head is inserted into said internal volume of said intermediate member, said screw head being rotatable at least at the times of assembly and implantation in bone within said internal volume of said intermediate member with three degrees of freedom.

22. The device of claim 21, wherein said internal volume of said intermediate member includes a cylindrical portion defined by a cylindrical internal surface, wherein said cylindrical portion communicates with said upper opening of said internal volume of said intermediate member and said spherical portion communicates with said lower opening of said internal volume of said intermediate member.

23. The device of claim 21, wherein said intermediate member is made of a material that is resiliently deformable.

24. The device of claim 21, wherein said screw head includes a hole in said equatorial flat portion, and further comprising a set screw inserted in said hole so that a portion of said set screw extends out of said screw head to limit rotation of said screw head in said internal volume of said intermediate member.

25. An intervertebral linking device, comprising:
an elongated linking member having a first receiving portion, a second receiving portion and a body extending between said portions, said first receiving portion having an upper surface and a lower surface and an internal volume defined by a truncated spherical surface, said internal volume having an upper opening in said upper surface and a lower opening in said lower surface, each of said openings having a diameter, said internal volume having a maximum diameter between said openings, wherein said diameters of said upper and lower openings are smaller than said maximum diameter, an intermediate member having a top surface and a bottom surface and a truncated spherical external surface, said truncated spherical external surface having a top diameter at said top surface, a bottom diameter at said bottom surface and a maximum diameter between said top and bottom surfaces, wherein said top and bottom diameters are smaller than said maximum diameter of said truncated spherical external surface, wherein said intermediate member includes an internal volume with a spherical portion defined by a truncated spherical internal surface, said internal volume having an upper opening in said upper surface and a lower opening in said lower surface and a maximum diameter between said upper and lower openings, each of said openings having a diameter, said maximum diameter of said internal volume of said intermediate member being larger than said diameters of said upper and lower openings of said internal volume of said intermediate member, wherein said maximum diameter of said truncated spherical external surface is larger than said diameters of said upper and lower openings of said internal volume of said elongated linking member; and a screw having a head and a threaded shaft, said shaft extending along a longitudinal axis, said head being spherical with an equator of greatest diameter and including an equatorial flat portion passing through said equator, said equatorial flat portion lying oblique to said longitudinal axis, said head having a first diameter between spherical portions and a second diameter between parts of said equatorial flat portion that is less than said first diameter, said first diameter being substantially equal to said maximum diameter of said internal volume of said intermediate member, said first diameter being larger than said diameter of said lower opening of said internal volume of said intermediate member, and said second diameter being equal to said diameter of said lower opening of said internal volume of said intermediate member;

wherein said intermediate member is inserted into said internal volume of said elongated linking member, said intermediate being rotatable at least at the times of assembly and implantation in bone within said internal volume with three degrees of freedom, and said screw head is inserted into said internal volume of said intermediate member, said screw head being rotatable at least at the times of assembly and implantation in bone within said internal volume of said intermediate member with three degrees of freedom; and wherein said bottom surface of said intermediate member is angled from said truncated spherical exterior surface to said truncated spherical internal surface in a direction toward said top surface of said intermediate member.

* * * * *